United States Patent [19]

Muchowski et al.

[11] Patent Number: 4,803,269

[45] Date of Patent: * Feb. 7, 1989

[54] 4-MONOSUBSTITUTED AND 4,6-DISUBSTITUTED N-(α-PHENYLETHYL)PHENOXAZINES

[75] Inventors: Joseph M. Muchowski, Sunnyvale; Robert J. Greenhouse, Cupertino, both of Calif.; Angel Guzman, Mexico City, Mexico

[73] Assignee: Syntex (U.S.A.) Inc., Palo Alto, Calif.

[ * ] Notice: The portion of the term of this patent subsequent to Nov. 17, 2004 has been disclaimed.

[21] Appl. No.: 85,595

[22] Filed: Aug. 14, 1987

Related U.S. Application Data

[63] Continuation of Ser. No. 868,976, May 30, 1986, Pat. No. 4,707,473.

[51] Int. Cl.[4] .................... C07D 279/24; C07F 7/10
[52] U.S. Cl. ........................ 544/69; 544/73; 544/102; 544/103; 544/104
[58] Field of Search ................ 544/69, 73, 102, 103, 544/104

[56] References Cited

U.S. PATENT DOCUMENTS 4,666,907 5/1987 Fortin et al. .................... 544/102 X
4,707,473 11/1987 Muchowski .......................... 514/63

FOREIGN PATENT DOCUMENTS 138481 4/1985 European Pat. Off. .

OTHER PUBLICATIONS

Gilman et al., JACS, vol. 80, (1958), pp. 2195–2197.
Higginbottom et al., Chemical Abstracts, vol. 57, (1962), 4666d.
Brewster et al., Chemical Abstracts, vol. 89, (1976), 108617q.
Blank et al., J. Med. Chem., vol. 11, (1968), pp. 807–811.
McOmie, Protective Groups in Organic Chemistry, Plenum Press, New York, (1973), pp.

*Primary Examiner*—Richard L. Raymond
*Attorney, Agent, or Firm*—David A. Lowin; Tom M. Moran

[57] ABSTRACT

4-Monosubstituted and 4,6-disubstituted phenoxazines, methods of preparing them and pharmaceutical compositions containing them. These compounds are useful as anti-inflammatories.

21 Claims, No Drawings

4-MONOSUBSTITUTED AND 4,6-DISUBSTITUTED N-(α-PHENYLETHYL)PHENOXAZINES

This is a continuation of pending application Ser. No. 866,976, filed May 30, 1986, now U.S. Pat. No. 4,707,473, incorporated herein by reference.

BACKGROUND OF THE INVENTION

1. Field of the Invention

This invention relates to phenoxazines, particularly to 4-mono-substituted and 4,6-di-substituted phenoxazines, to methods of preparing them, to pharmaceutical compositions containing them and to the use of them as anti-inflammatories. These compounds are lipoxygenase inhibitors.

2. Relevant Art

European Patent Application No. 0138481 teaches a generic class of phenothiazine compounds useful as leukotriene biosynthesis inhibitors. The specification teaches the substitution of the sulfur atom in the heterocyclic ring with oxygen, thereby producing phenoxazine. Many phenoxazine compounds are disclosed, but none are substituted solely at the 4 position or disubstituted at the 4,6 positions.

In J. Am. Chem. Soc., 80, 2195 (1958) Gilman reports the synthesis phenoxazine-4-carboxylic acid by reacting phenoxazine with n-butyl lithium and then carbon dioxide.

Blank et at, J. Med. Chem., 11, 807 (1968) reports that Gilman's report of phenoxazine-4-carboxylic acid was apparently in error. Based on an analysis of unambiguously synthesized material, Blank demonstrated that Gilman's compound was phenoxazine-1-carboxylic acid. Therefore, despite reports to the contrary, phenoxazine-4-carboxylic acid has not been prepared.

SUMMARY OF THE INVENTION

An aspect of this invention is a compound represented by the formula:

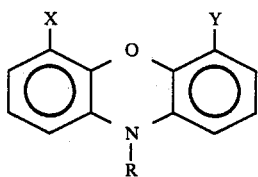

where:
R is a protecting group or hydrogen;
X is alkyl, hydroxyalkyl, alkylthio, haloalkyl, C(O)R$^1$, CH$_2$NR$^2$R$^3$, SiR$_2^4$R$^5$;
  where R$^1$ is hydrogen, hydroxy, alkyl, alkoxy, aryl, aryloxy, or amino;
  R$^2$ and R$^3$ are independently hydrogen or alkyl, or NR$^2$R$^3$R$^2$ together represent a heterocyclic ring having from four to seven members and containing no more than one hetero-atom additional to the nitrogen of NR$^2$R$^3$R$^2$; and
  R$^4$ is lower alkyl or phenyl; and
  R$^5$ is lower alkyl;
Y is the same as X or hydrogen; and the pharmaceutically acceptable salts thereof.

A further aspect of the present invention is the method of making compounds of formula (A) as herinafter described.

A further aspect of the present invention is a pharmaceutical formulation comprising a therapeutically effective amount of a compound of formula (A) and a pharmaceutically acceptable excipient.

A further aspect of the present invention is a method of treating a mammal having a disease state characterized by overproduction of the products of lipoxygenase metabolism of arachidonic acid, which method comprises administering a therapeutically effective amount of a compound of formula (A) to the mammal.

DETAILED DESCRIPTION OF THE INVENTION

Definitions

As used in this specification the term "alkyl" means a branched or unbranched saturated hydrocarbon radical having up to 12 carbon atoms. Examples include methyl, ethyl, propyl, t-butyl, n-pentyl, n-hexyl, octyl, dodecyl, and the like.

As used in this specification the term "alkoxy" means the group —OR wherein R is alkyl as defined above. Examples include methoxy, ethoxy, propoxy, t-butoxy, n-pentyloxy, n-hexyloxy, octyloxy, dodecyloxy, and the like.

As used in this specification the term "alkylthio" means the group —SR wherein R is alkyl as defined above. Examples include, methylthio, ethylthio, propylthio, t-butylthio, n-pentylthio, n-hexylthio, octylthio, dodecylthio, and the like.

As used herein the term "lower" as used herein, modifies alkyl, alkoxy, and alkylthio, and refers to those radicals having six carbon atoms or less.

As used in this specification the term "hydroxyalkyl" means —(CH$_2$)$_n$OH where n can be an integer from 1 to 6. Examples include hydroxymethyl, hydroxyethyl, hydroxypropyl, and hydroxyhexyl. In the present invention the particularly preferred hydroxyalkyl compounds are those where the hydroxy group is attached to the α-carbon atom, for example, hydroxymethyl and 1-hydroxypropyl.

As used in this specification the term "halo" means chloro, bromo, and iodo.

As used in this specification the term "haloalkyl" means —(CH$_2$)$_n$X where n can be an integer from 1 to 6 and X is halo, as defined above.

As used in this specification the term "protecting group" means any sterically bulky group that can be placed on the nitrogen of the phenoxazine molecule and removed without affecting the remainder of the phenoxazine molecule. The phenoxazine must have a protecting group during the reaction with an alkyl lithium compound, the reaction referred to, hereinafter, as "lithiation". Preferred protecting groups will be relatively less reactive to the lithiation than the phenoxazine molecule. Examples of preferred protecting groups include α-phenylethyl and sterically hindered silyl groups, for example, trimethylsilyl, triethylsilyl, triisopropylsilyl, t-butyldimethylsilyl, and the like.

As used in this specification the term "protected" means that the protection group is bonded to the nitrogen. The directing effect of the group substituted on the nitrogen is primarily a result of the 1-position on the phenoxazine being blocked by the protecting group. The work by Blank, previously referred to, indicates that the 1-position is the preferred site for lithiation in the unsubstituted phenoxazine system.

As used herein the term "optional" or "optionally" means that the subsequently described event or circumstance may or may not occur, and that the description includes instances where said event or circumstance occurs and instances in which it does not.

As used in this specification the term "aryl" refers to optionally substituted phenyl or optionally substituted benzyl, wherein the optional substituents are alkyl, alkoxy, or halo.

The term "treatment" as used herein covers any treatment of a disease in a mammal, and includes:

(i) preventing the disease, that is, causing the clinical symptoms of the disease not to develop;

(ii) inhibiting the disease, that is, arresting the development of clinical symptoms; or (iii) relieving the disease, that is, causing regression of clinical symptoms.

As used herein the term "pharmaceutically acceptable salts" refers to those salts which retain the biological effectiveness and properties of the neutral parent compounds and which are not biologically or otherwise undesirable. In the compounds of this invention the substituents at positions 4 and 6 may be either a carboxylic acid or a basic amine. Therefore the compounds of this invention may form base or acid addition salts.

Pharmaceutically acceptable acid addition salts may be formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

Pharmaceutically acceptable salts may be formed from carboxylic acids on position 4 or 6. Examples of bases that form acceptable salts include sodium hydroxide, potassium hydroxide, and ammonium hydroxide. Organic bases such as caffine, procaine, and pyridine are also useful in forming salts with the carboxylic acids of this invention.

Pharmaceutically acceptable salts can be prepared by conventional procedures, e.g. by reacting an organic solution of the compound with a solution of a suitable acid to obtain an acid addition salt either by precipitation, or by evaporation of the solution. In the case of ester starting materials, often the acid used will cause hydrolysis to the free acid in addition to salt formation.

Currently Preferred Embodiments of the Invention

The currently preferred embodiments of the present invention include compounds represented by formula (A) and includes those compounds where X is methyl; hydroxymethyl; methylthio; methylchloro; formyl; carboxy; methoxycarbonyl; morpholinomethyl; dimethylaminomethyl; and trimethylsilyl; when Y is the same as X or hydrogen; and R is α-phenylethyl or t-butyldimethylsilyl or hydrogen; and the pharmaceutically acceptable salts thereof.

In those instances where R is a protecting group, the compounds of this invention may be referred to as formula (A'), and in those instances where R is hydrogen, the compounds of this invention may be referred to as formula (A").

Utility and Administration

The compounds of this invention are useful for treating mammals having a variety of disease states characterized by overproduction of the products of the lipoxygenase metabolism of arachidonic acid. Disease states that may be treated include inflammatory diseases including rheumatoid arthritis, inflammatory bowel disease; psoriasis; various cardiovascular syndromes, particularly those characterized by inappropriate clotting of the blood, such as thrombosis, and the like; and hypersensitivity diseases, such as asthma.

Generally, the diseases characterized by overproduction of the products of the lipoxygenase metabolism of arachidonic acid are found in mammals including domestic commercial animals such as horses, cattle, sheep and pigs; domestic house animals such as dogs, cats and the like; and particularly humans.

In vitro lipoxygenase inhibiting activity of the compounds of this invention are determined by the standard Human Polymorphonuclear Leukocytes assay. This assay is a modification of that described by O. Radmark, C. Malmasten, and B. Samuelsson in *Febs Letters*, 110, 213–215 (1980). In vivo lipoxygenase inhibiting activity of the compounds of this invention are determined by the rat ear croton oil inflammation assay as that described by G. Tonelli, L. Thidould, and I. Ringler in *Endocrinology*, 77, 625–634 (1965).

The compounds of this invention are administered at a therapeutically effective dosage, i.e. a dosage sufficient to inhibit the activity of lipoxygenase. Administration of the active compounds and salts described herein can be via any of the accepted modes of administration for agents which are anti-inflammatory agents. Depending on the specific disease state, administration can be systemic, via parenteral, oral, intravenous, or nasal routes; or topical.

The compounds of this invention are generally administered as a pharmaceutical composition which comprises a pharmaceutical excipient in combination with a compound of formula (A). Depending on the type of composition, the compound of formula (A) is present in an amount ranging from about 0.5 wt% to 95.0 wt% with an excipient in the range of about 99.5 wt% to 5.0 wt%

For solid compositions, conventional nontoxic solid carriers include, for example, pharmaceutical grades of mannitol, lactose, starch, magnesium stearate, sodium saccharin, talcum, cellulose, glucose, sucrose, magnesium carbonate, and the like may be used. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate; triethanolamine oleate, etc. Actual methods of preparing such dosage forms are known, or will be apparent, to those skilled in this art; for example, see *Remington's Pharmaceutical Sciences*, Mack Publishing Company, Easton, Pa., 18th Edition, 1975. The composition or formulation to be administered will, in any event, contain a quantity of the active compound(s) in an amount effective to alleviate the symptoms of the subject being treated.

For oral administration, a pharmaceutically acceptable nontoxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 25–70%.

For systemic administration via suppository, traditional binders and carriers include, e.g. polyalkalene glycols or triglycerides. Such suppositories may be formed from mixtures containing active ingredient in the range of 0.5%–10%; preferably 1–2%.

Methods of Preparation

The compounds of this invention can be made as shown in REACTION SCHEME I.

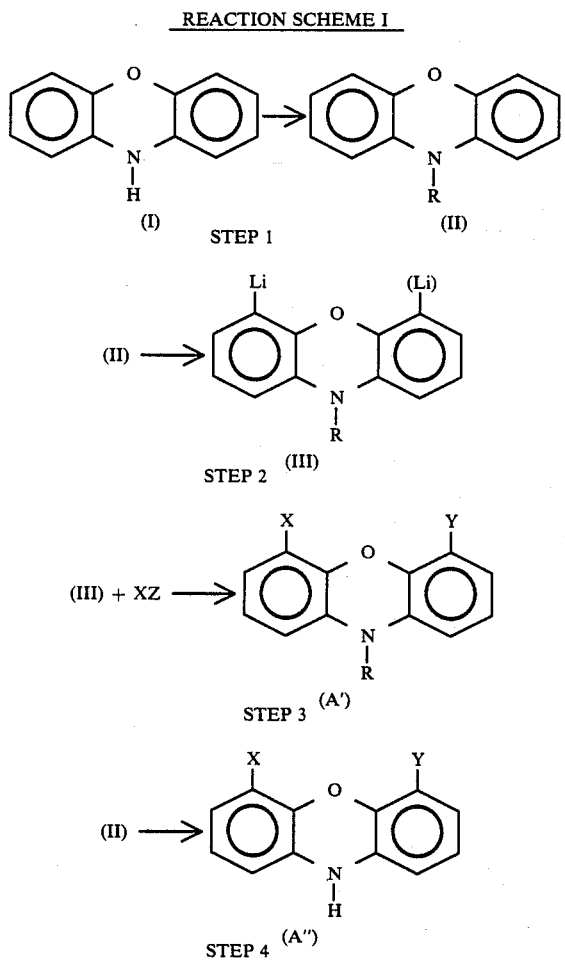

where X, Y, and R all have the meanings as defined in the Summary of the Invention above.

In STEP 1, phenoxazine (I) is dissolved in an inert polar solvent, preferably dimethylformamide, and reacted with a protecting group, for example, α-phenylethyl bromide. The reaction is done in the presence of an alkali metal hydride, preferably sodium hydride, and forms the protected phenoxazine (II).

In STEP 2, compound (II) is dissolved in an inert solvent, preferably an etheral solvent, for example tetrahydrofuran, and reacted with an alkyl lithium, for example, n-butyl lithium in hexane solution, at 0° C. to −30° C. The reaction is completed in from 0.25 hours to about 6 hours, typically about 1 hour for the mono-lithiated compound and about 4 hours for the di-lithiated compounds. By varying the molar ratio of n-butyl lithium to compound (II) mono-lithiated compounds, represented in the reaction scheme as Li, or di-lithiated compounds, represented in the reaction scheme with the additional (Li), can be formed. It has been found that a 1.2 molar ration gives the mono-lithiated compound in good yield and a 2.2 molar ratio gives the di-lithiated compound in good yield.

In STEP 3, an electrophile, XZ, where X as defined above, and Z is the leaving group, is added to the solution of the lithiated species, to form the electrophile-substituted species (III). Depending on the physical properties of XZ, it can be added neat, as a liquid or solid; dissolved in a suitable inert solvent, preferably the solvent chosen for the lithiation reaction; or, in the case of gaseous XZ, for example, carbon dioxide, bubbled through the reaction mixture. A representative selection of various XZ are shown in Table 1, together with the radicals that add onto the phenoxazine.

TABLE 1

| XZ | Radical Added to Phenoxazine |
| --- | --- |
| alkylhalide | alkyl |
| benzylhalide | benzyl |
| $R^6SSR^6$; where $R^6$ is lower alkyl, benzyl, or phenyl | $SR^6$ |
| carbon dioxide as gas or solid | carboxylic acid |
| dimethylformamide | C(O)H |
| $R_7C(O)R^8$; where $R^7$ and $R^8$ can be the same or different, and can be hydrogen, lower alkyl, benzyl, or phenyl | $CR^7R^8OH$ |
| elemental halogen | halo |
| trialkylsilylhalide | trialkylsilyl |

This reaction forms the 4-substituted or 4,6-disubstituted N-protected phenoxazine (A').

Compound (A') may be further reacted to vary the form of the substituent on the phenoxazine. For example, the oxidation state of the substituent may be changed. For example, a carbonyl group, such as that in a formyl group, may be reduced, by a metal hydride, for example, sodium borohydride, to an alcohol, in this case the hydroxymethyl alcohol. The resulting alcohol may be reacted further, for example, with thionyl chloride and the resulting unstable chloromethyl compound reacted with a dialkylamine, for example, dimethylamine, forming the dialkylaminomethyl derivative, in this case the dimethylaminomethyl derivative. Another example of further reacting (A') is the derivatization of carboxylic acids, by conventional means, to make salts and esters or the derivatization of amino groups to make acid addition salts.

Compound (A') may be deprotected, thereby forming the compound (A″), by any of several preferred methods.

Compound (A') may be catalytically reduced using a noble metal catalyst, preferably palladium on charcoal, in the presence of gaseous hydrogen. Compound (A') is dissolved in a suitable inert solvent, for example, an alcohol, preferably, ethanol, then contacted with the catalyst, and the mixture contacted with a hydrogen atmosphere. Although the hydrogen pressure may be at greater than ambient pressure, the preferred pressure is ambient.

Alternatively, (A') may be deprotected using a metal that reacts with a protic acid to form molecular hydrogen in situ, for example, zinc in the presence of acetic or hydrochloric acid. This second process is used when the electrophilic fragment, X and Y, interferes with the catalytic reaction or the electrophilic fragment, itself, is sensitive to catalytic reduction. For example, $R^1S$ will poison a palladium catalyst.

The third method requires the use of a different protecting group than the N-α-phenylethyl group. If the electrophile is sensitive to a catalytic reduction and to zinc/acid reduction, for example, as formyl is, it may be preferable to protect the phenoxazine nitrogen with a silane protecting group, for example t-butyldimethylchlorosilane. Then the protecting group can be removed under nonreducing conditions.

PREPARATION 1

N-α-Phenylethylphenoxazine

A. A solution of phenoxazine 76 g, 0.417 mol (Aldrich Chemical Co., Milwaukee, WI, Cat. No. P1,585-8) in dry dimethylformamide (120 ml) was added to a stirred suspension of sodium hydride (22 g, 0.458 mol, 50% suspension in mineral oil) in dry dimethylformamide (500 ml). After 1 hour at room temperature α-phenylethyl chloride (59 g, 0.43 mol) was added dropwise and when the addition was completed, stirring was continued for another 30 min. The solution was poured into water, the product extracted with ethyl acetate, the extract washed with water, and dried over sodium sulfate. The solvent was removed under reduced pressure. N-α-Phenylethylphenoxazine was crystallized from ether-hexane, mp 100° C.

PREPARATION 2

N-t-Butyldimethylsilylphenoxazine

A. 5 Grams of phenoxazine was dissolved in 100 ml of dry tetrahydrofuran, then 1.63 g of 50% sodium hydride in mineral oil was added and the mixture refluxed for 30 minutes. Then 6.19 g of t-butyldimethylsilyl chloride in dimethylformamide (2 ml) and tetrahydrofuran (8 ml) was added and reflux was continued for five more minutes. The reaction was quenched by the addition of water, the organic layer was separated and dried over sodium sulfate. Then the solvent was removed under reduced pressure and the residue purified by column chromatography (silica as solid phase, hexane:ethylacetate (95:5) as mobile phase). N-t-butyldimethylsilylphenoxazine had a melting point of 57° C. after crystallization from pentane.

EXAMPLE 1

4-Methyl-N-(α-phenylethyl)phenoxazine

A. 2.87 g (10 mmoles) of N-(α-phenylethyl)phenoxazine were dissolved, under nitrogen atmosphere, in 100 ml of dry tetrahydrofuran. The solution was cooled to −20° C. and 7.2 ml of a 1.67N solution of n-butyllithium (12 mmoles) in hexane was added thereto. The resulting mixture was stirred for 1 hour at −20° C. and then treated with 1.7 g (12 mmoles, 0.74 ml) of methyl iodide. Stirring was continued for an additional hour at the same temperature. The reaction solution was then poured into water (200 ml) and extracted with ethyl acetate (2×50 ml). The combined extracts were dried over sodium sulfate and the solvent removed under reduced pressure. The oily residue (2.96 g) was purified by thin layer chromatography (TLC) using hexane as solvent, to yield:

4-methyl-N-(α-phenylethyl)phenoxazine, as an oil; ir: 2925; 2875; 1603 cm$^{-1}$: nmr: (CDCl$_3$) 1.80 ppm (d, 3H), 2.23 ppm (s, 3H), 7.17 ppm (c, 1H), 6.20–6.80 ppm (m, 7H), 7.60 ppm (m, 5H).

B. Similarly, by following the procedure of Part A of this Example, but replacing methyl iodide with:
carbon dioxide (as either gas bubbled through or solid added to the solution)
trimethylchorosilane;
dimethyldisulfide
dimethylformamide;
ethyliodide;
n-hexyliodide;
diethyldisulfide;
di-n-hexyldisulfide;
N,N-dimethylacetamide;
N,N-dimethyldimethylpropionamide one can obtain:
N-(α-phenylethyl)phenoxazine-4-carboxylic acid;
4-trimethylsilyl-N-(α-phenylethyl)phenoxazine, an oil, ir: (neat) 3065, 2960, 1595, 1488 cm$^{-1}$;
4-methylthio-N-(α-phenylethyl)phenoxazine, an oil, ir: (CHCl$_3$) 2940, 1590 cm$^{-1}$; nmr: (CDCl$_3$) 2.40 ppm (s, 3H), 5.20 ppm (c, 1NH), 6.10–6.20 ppm (m, 7H);
4-formyl-N-(α-phenylethyl)phenoxazine, mp 204°–205° C.;
4-ethyl-N-(α-phenylethyl)phenoxazine;
4-n-hexyl-N-(α-phenylethyl)phenoxazine;
4-ethylthio-N-(α-phenylethyl)phenoxazine;
4-n-hexylthio-N-(α-phenylethyl)phenoxazine;
4-acetyl-N-(α-phenylethyl)phenoxazine; and
4-propionyl-N-(α-phenylethyl)phenoxazine.

C. Similarly, by following the procedure of Part A of this Example, but replacing N-(α-phenylethyl)phenoxazine with N-t-butyldimethylsilylphenoxazine and replacing methyl iodide with:
carbon dioxide;
trimethylchorosilane;
dimethyldisulfide
dimethylformamide;
ethyliodide;
n-hexyliodide;
diethyldisulfide;
di-n-hexyldisulfide; and
N,N-dimethylacetamide, one can obtain:
N-(t-butyldimethylsilyl)phenoxazine-4-carboxylic acid, an oil; nmr: (CDCl$_3$) 0.30 ppm (s, 6H), 0.40 ppm (s, 9NH), 6.95 ppm (m, 7H);
4-trimethylsilyl-N-(t-butyldimethylsilyl)phenoxazine;
4-methylthio-N-(t-butyldimethylsilyl)phenoxazine;
4-formyl-N-(t-butyldimethylsilyl)phenoxazine, mp 61°–62° C.;
4-ethyl-N-(t-butyldimethylsilyl)phenoxazine;
4-n-hexyl-N-(t-butyldimethylsilyl)phenoxazine,
4-ethylthio-N-(t-butyldimethylsilyl)phenoxazine,
4-n-hexylthio-N-(t-butyldimethylsilyl)phenoxazine, and
4-acetyl-N-(t-butyldimethylsilyl)phenoxazine.

EXAMPLE 2

4-Methylthiophenoxazine

A. 1 g of zinc dust was added to a stirred solution of 1.9 g of 4-methylthio-N-(α-phenylethyl)phenoxazine in 50 ml of glacial acetic acid. Thereafter, 3 ml of concentrated hydrochloric acid was added, in dropwise fashion. The reaction mixture was stirred at room temperature for 5 minutes, after which time the reaction was complete, as demonstrated by TLC analysis. [hexane-ethyl acetate 80–20]. The reaction mixture was then poured into water and extracted with ethyl acetate; the combined extracts were dried and the solvent removed under reduced pressure. Purification of the residue on 80 g of a silica gel column, using hexane-ethyl acetate (80:20) as the eluant afforded 4-methylthiophenoxazine as a white solid, which was recrystallized from ether-hexane, mp 115° C.

B. Similarly, by following the procedure of Part A. this Example but replacing:
4-methylthio-N-(α-phenylethyl)phenoxazine with:
  N-(α-phenylethyl)phenoxazine-4-carboxylic acid
  4-trimethylsilyl-N-(α-phenylethyl)phenoxazine;
  4-ethyl-N-(α-phenylethyl)phenoxazine;
  4-n-hexyl-N-(α-phenylethyl)phenoxazine;
  4-ethylthio-N-(α-phenylethyl)phenoxazine; and
  4-n-hexylthio-N-(α-phenylethyl)phenoxazine, one can obtain:
    phenoxazine-4-carboxylic acid, mp 181°–182° C.;
    4-trimethylsilylphenoxazine;
    4-ethylphenoxazine;
    4-n-hexylphenoxazine;
    4-ethylthiophenoxazine; and
    4-n-hexylthiophenoxazine.

EXAMPLE 3

4-Methylphenoxazine

A. A solution of 1.5 g of:
4-methyl-N-(α-phenylethyl)phenoxazine in 30 ml of ethyl acetate and 130 ml of ethanol was hydrogenated at atmospheric pressure (585 mm Hg) in the presence of 1.5 g of 10% palladium-charcoal as catalyst, until the calculated amount of hydrogen was consumed (16 hours). The catalyst was then separated by filtration through celite and the solvent removed under reduced pressure. Chromatography of the solid residue (1 g) on 100 g of silica gel in a column, using hexane-ethyl acetate (80:20) as the eluting solvent produced 4-methylphenoxazine, a white solid, which was recrystallized from pentane, mp: 91° C.

B. Similarly, by following the procedure of Part A. this Example but using:
N-(α-phenylethyl)phenoxazine-4-carboxylic acid
4-trimethylsilyl-N-(α-phenylethyl)phenoxazine;
4-formyl-N-(α-phenylethyl)phenoxazine;
4-ethyl-N-(α-phenylethyl)phenoxazine;
4-n-hexyl-N-(α-phenylethyl)phenoxazine;
4-ethylthio-N-(α-phenylethyl)phenoxazine;
4-n-hexylthio-N-(α-phenylethyl)phenoxazine; and
4-acetyl-N-(α-phenylethyl)phenoxazine, as a starting material one can obtain:
  phenoxazine-4-carboxylic acid, mp 181°–182° C.;
  4-trimethylsilylphenoxazine;
  4-formylphenoxazine;
  4-ethylphenoxazine;
  4-n-hexylphenoxazine;
  4-ethylthiophenoxazine;
  4-n-hexylthiophenoxazine; and
  4-α-hydroxymethylphenoxazine.

EXAMPLE 4

4-Formylphenoxazine

A. 200 Milligrams of:
4-formyl-N-(t-butyldimethylsilyl)phenoxazine was dissolved in 40 ml of tetrahydrofuran, the mixture was heated to 40° C. and then 234 mg of tetrabutylammonium fluoride was added and the reaction mixture cooled after five minutes. The product was washed with water the solvent, dried and removed and the product purified by column chromatography (silica as solid support and dichloromethane as mobile phase). A solid with mp 181°–182° C. was obtained after crystallization from ethyl acetate:hexane.

B. Similarly, by following the procedure of Part A above, but replacing:
4-formyl-N-(t-butyldimethylsilyl)phenoxazine with:
  N-(t-butyldimethylsilyl)phenoxazine-4-carboxylic acid;
  4-trimethylsilyl-N-(t-butyldimethylsilyl)phenoxazine;
  4-methylthio-N-(t-butyldimethylsilyl)phenoxazine;
  4-ethyl-N-(t-butyldimethylsilyl)phenoxazine;
  4-n-hexyl-N-(t-butyldimethylsilyl)phenoxazine,
  4-ethylthio-N-(t-butyldimethylsilyl)phenoxazine,
  4-n-hexylthio-N-(t-butyldimethylsilyl)phenoxazine, and
  4-acetyl-N-(t-butyldimethylsilyl)phenoxazine one can obtain:
    phenoxazine-4-carboxylic acid, 181°–182° C.;
    4-trimethylsilylphenoxazine, 81.5° C.;
    4-methylthiophenoxazine, mp 115° C.;
    4-ethylphenoxazine;
    4-n-hexylphenoxazine,
    4-ethylthiophenoxazine,
    4-n-hexylthiophenoxazine, and
    4-acetylphenoxazine.

EXAMPLE 5

4-Hydroxymethyl-N-(α-phenylethyl)phenoxazine

A. A mixture of 3.9 g (12.3 mmoles) of 4-formyl-N-(α-phenylethyl)phenoxazine, 250 ml of ethanol and 0.594 g (18.5 mmoles) of sodium borohydride was heated at 40° C. under stirring during 15 minutes. The solvent was then removed under reduced pressure and the residue diluted with water and extracted with ethyl acetate (2×100 ml). The combined extracts were dried and the solvent removed under reduced pressure. The oily residue (3.5 g) was percolated through a short column of silica gel using ether as the solvent, to yield 4-hydroxymethyl-N-(α-phenylethyl)phenoxazine, as an oil ir: ($CDCl_3$) 3610, 3620, 3200, 3000, 2940, 2880, 1595 $cm^{-1}$.

B. Similarly, by following the procedure of Part A above, but replacing:
4-formyl-N-(α-phenylethyl)phenoxazine with:
  4-acetyl-N-(α-phenylethyl)phenoxazine; and
  4-propionyl-N-(α-phenylethyl)phenoxazine one can obtain:
    4-(1-hydroxyethyl)-N-(α-phenylethyl)phenoxazine; and
    4-(1-hydroxypropyl)-N-(α-phenylethyl)phenoxazine.

EXAMPLE 6

4-(Chloromethyl)-N-(α-phenylethyl)phenoxazine

A. 0.3 Milliliters (4.1 mmoles) of thionyl chloride was added, under nitrogen, to a solution of 1.22 g (3.82 mmoles) of:

4-hydroxymethyl-N-(α-phenylethyl)phenoxazine (Example 4) dissolved in 50 ml of dry methylene chloride. The reaction mixture was stirred at room temperature under anhydrous conditions for 1 hour and the solvent removed under vacuo, to yield a solution of (4-chloromethyl-N-α-phenylethyl)phenoxazine, an unstable product which was used in the next step without further purification.

EXAMPLE 7

4-(Dimethylaminomethyl)-N-(α-phenylethyl)phenoxazine

A. A solution of 4-chloromethyl-N-(α-phenylethyl)-phenoxazine in 4 ml of methylene chloride was rapidly poured into 50 ml of liquid dimethylamine, at −70° C. The reaction mixture was stirred at −70° C. for 30 minutes. Then, the excess reagent and solvent were removed by heating the reaction mixture to 40° C. The residue was purified by column chromatography on 105 g of silica gel, using hexane:ethyl acetate (60:40) as eluant, thus obtaining:

4-(dimethylaminomethyl)-N-(α-phenylethyl)phenoxazine, as an oil: ir: 3005, 2965, 2940, 1595, 1574 cm$^{-1}$: nmr: (CDCl$_3$) 1.83–1.90 ppm (d, 3H), 2.39 ppm (s, 6H), 5.23 ppm (c, 1H), 6.25–6.53 ppm (m, 2H), 6.53–6.83 ppm (m, 5H), 7.38 ppm (m, 5H).

B. Similarly, by following the procedure of Part A above, but replacing dimethylamine with:
diethylamine;
dibutylamine; and
ethylbutylamine one can obtain:
4-(diethylaminomethyl)-N-(α-phenylethyl)phenoxazine;
4-(dibutylaminomethyl)-N-(α-phenylethyl)phenoxazine; and
4-(ethylbutylaminomethyl)-N-(α-phenylethyl)phenoxazine.

EXAMPLE 8

4-(Dimethylaminomethyl)phenoxazine

A. 1 g of zinc dust was added to a stirred solution of 2 g of:

4-(dimethylaminomethyl)-N-(α-phenylethyl)phenoxazine in 150 ml of glacial acetic acid. Then 6 ml of concentrated hydrochloric acid was slowly added, at room temperature. The course of the reaction was followed by TLC. After 10 minutes the reaction appeared to be completed. It was then poured into water (500 ml) and enough 25% aqueous sodium hydroxide solution was added to bring the pH to 9. The product was then extracted with ethyl acetate (3×100 ml). The combined extracts were washed with water (3×200 ml), dried and the solvent removed under reduced pressure. The residue (1.41 g) was purified by column chromatography on 80 g of silica gel, using hexane-ethyl acetate (60:40) as eluant, thus obtaining 4-(dimethylaminomethyl)phenoxazine, which was recrystallized from ethyl acetate:hexane, mp 120° C.

B. Similarly, by following the procedure of Part A above, but replacing:
4-(dimethylaminomethyl)-N-(α-phenylethyl)phenoxazine with:
4-(diethylaminomethyl)-N-(α-phenylethyl)phenoxazine;
4-(dibutylaminomethyl)-N-(α-phenylethyl)phenoxazine; and
4-(ethylbutylaminomethyl)-N-(α-phenylethyl)-phenoxazine as the starting material one can obtain:
4-(diethylaminomethyl)phenoxazine;
4-(dibutylaminomethyl)phenoxazine; and
4-(ethylbutylaminomethyl)phenoxazine.

EXAMPLE 9

4-(Morpholinomethyl)-N-(α-phenylethyl)phenoxazine

A. 1.22 Grams (3.82 mmoles) of 4-hydroxymethyl-N-(α-phenylethyl)phenoxazine (Example 4) were converted into the 4-chloromethyl-N-(α-phenylethyl)-phenoxazine (Example 6). The crude product was immediately dissolved in 25 ml of anhydrous methylene chloride, under nitrogen, and to the resulting solution 2 g (23 mmoles) of morpholine were added. The reaction mixture was stirred for 3 hours at room temperature and poured into water. The organic phase was separated, washed with water, dried and the solvent removed under reduced pressure, to yield 1.53 g of a brown oil, which was purified by column chromatography on 75 g of silica gel using hexane-ethyl acetate (60:40) as eluant, thus obtaining the pure compound, as a yellow oil.

ir: 3005, 2465, 2940, 2595, 1573 cm$^{-1}$: nmr: (CDCl$_3$) 1.80–1.86 ppm (d, 3H), 2.53 ppm (s, 4H), 3.56 ppm (s, 2H), 3.70 ppm (m, 4H), 5.23 ppm (m, 1H), 6.23–6.50 ppm (m, 2H), 6.50–6.80 ppm (m, 5H), 7.35 ppm (m, 5H).

B. Similarly, by following the procedure of Part A above, but replacing morpholine with:
pyrrolidine; and
piperidine, instead of morpholine one can obtain:
4-(pyrrolidinomethyl)-N-(α-phenylethyl)phenoxazine; and
4-(piperidinomethyl)-N-(α-phenylethyl)phenoxazine.

EXAMPLE 10

4-(Morpholinomethyl)phenoxazine hydrochloride

A. 1.5 g of zinc dust was added to a stirred solution of 3 g of:

4-(morpholinomethyl)-N-(α-phenylethyl)phenoxazine (Example 8) in 200 ml of glacial acetic acid. This was followed by the slow addition of 7.5 ml concentrated hydrochloric acid. The reaction mixture was stirred at room temperature for 10 minutes, when TLC analysis [hexane-ethyl acetate (60:40)] showed the reaction to be essentially complete. The reaction mixture was then poured onto 500 ml of water, 25% aqueous sodium hydroxide was added until a pH-9 was obtained and the alkaline solution extracted with ethyl acetate (3×100 ml). The combined extracts were washed with water to neutrality, dried and the solvent was removed. The crude 4-(morpholinomethyl)-phenoxazine is unstable and therefore was immediately converted into the hydrochloride by dissolving it in a saturated solution of hydrochloric acid in methanol until a pH-3 was reached. The solvent was then eliminated under vacuo and the solid residue purified by recrystallization from methanol-ether, thus obtaining 4-(morpholinomethyl)phenoxazine hydrochloride, mp 120° C.

B. Similarly, by following the procedure of Part A of the preparation above but replacing:
4-(morpholinomethyl)-N-(α-phenylethyl)phenoxazine with:
- 4-(pyrrolidinomethyl)-N-(α-phenylethyl)phenoxazine; and
- 4-(piperidinomethyl)-N-(α-phenylethyl)phenoxazine one can obtain:
- 4-(pyrrolidinomethyl)phenoxazine; and
- 4-(piperidinomethyl)phenoxazine.

EXAMPLE 11

N-(α-Phenylethyl)phenoxazine-4-carboxylic acid and N-(α-Phenylethyl)phenoxazine-4,6-carboxylic acid and their Methyl Esters A. A solution of N-(α-phenylethyl)phenoxazine (8.0 g, 27.8 mmol) in anhydrous tetrahydrofuran (125 ml) was cooled to −20° C. in a nitrogen atmosphere and 1.53N n-butyl lithium solution in hexane (21.8 ml, 33.4 mmol) was added dropwise. After stirring for 1 hour at −20° C., dry carbon dioxide was passed through the solution until the deep red color of the 4-lithio derivative had disappeared. The reaction mixture was left at −20° C. for 1 hour and then the solvent was removed under reduced pressure. Dilute sodium hydroxide solution was added to the residue and unreacted phenoxazine was extracted with ether. The aqueous alkaline phase was then made acidic with 20% hydrochloric acid and the products were extracted into ethyl acetate. The extract was washed with water, dried over sodium sulfate and evaporated in vacuo. The mixture of crude N-(α-phenylethyl)phenoxazine-4-carboxylic acid and N-(α-phenylethyl)phenoxazine-4,6-carboxylic acid was used without further purification.

B. The crude mixture was dissolved in dichloromethane and an excess of ethereal diazomethane was added. The solvent was removed in vacuo and the residue was subjected to column chromatography on silica gel (150 g) using ethyl acetate:hexane (1:9) as the eluting solvent. The monoester (1.25 g, 12%) and the diester (0.46 g, 5%). No N-(α-phenylethyl)phenoxazine-1-carboxylic acid was present in the product mixture as indicated by direct TLC comparison. Methyl N-(α-phenylethyl)phenoxazine-4-carboxylate was an oil, nmr: (CDCl$_3$) 1.87 ppm (d, 3H), 3.95 ppm (s, 3H), 5.18 ppm (q, 1H), 6.45–6.90 ppm (m, 4H), 7.10–7.25 ppm (m, 3H), 7.40 ppm (s, 5H). Dimethyl N-(α-phenylethyl)phenoxazine-4,6-dicarboxylate had a melting point, after recrystallization from ethyl acetate:hexane, of 102°–103° C.

EXAMPLE 12

Methyl phenoxazine-4-carboxylate

A. To 1.25 g of methyl N-(α-phenylethyl)phenoxazine-4-carboxylate in 25 ml of glacial acetic acid was added 500 g of zinc dust with stirring. To this stirred mixture, concentrated hydrochloric acid (2 ml) was added dropwise over a 5 minute period. At this time examination of the reaction mixture by TLC [silica gel, hexane:ethyl acetate (1:9)] showed that the starting material was consumed. The mixture was poured onto water, extracted with ethyl acetate, the extracted material was dried over sodium sulfate and the solvent removed under reduced pressure. Column chromatographic purification of the residue on silica gel (150 g) gave using the solvent system described above as the eluant gave a yellow solid, methyl phenoxazine-4-carboxylate, having mp 113°–114° C. after recrystallization from ethyl ether.

B. Similarly, by following the procedure of Part A of the preparation above but replacing methyl N-(α-phenylethyl)phenoxazine-4-carboxylate with dimethyl N-(α-phenylethyl)phenoxazine-4,6-dicarboxylate one obtains dimethyl phenoxazine-4,6-dicarboxylate, mp 145°–146° C.

EXAMPLE 13

Phenoxazine-4-carboxylic acid

A. A solution of methyl phenoxazine-4-carboxylate (0.241 g, 1 mmol) in methanol (25 ml) containing potassium hydroxide (0.560 g) was heated at reflux for 1 hour. The solvent was removed in vacuo and 5% hydrochloric acid added to the residue. The product was extracted with ethyl acetate, washed with water, dried over sodium sulfate and the solvent removed under reduced pressure. The solid residue was homogeneous by TLC over silica gel (ethyl acetate:hexane 1:3) and was different from the monocarboxylic acid described by Gilman and Moore. After recrystallization from benzene:ethyl ether phenoxazine-4-carboxylic acid, mp 181°–182° C. was obtained.

B. Similarly, by following the procedure of Part A of the preparation above but replacing methyl phenoxazine-4-carboxylate with dimethyl phenoxazine-4,6-dicarboxylate, one obtains phenoxazine-4,6-dicarboxylic acid, mp 146° C.

EXAMPLE 14

4,6-Dimethyl-N-(α-phenylethyl)phenoxazine

A. A solution of 10 g (34 mmoles) of N-(α-phenylethyl)phenoxazine in 100 ml of anhydrous tetrahydrofuran, under nitrogen, was cooled to −78° C. in a dry ice-acetone bath. 82 ml of a 1.4N solution (114 mmoles) of n-butyl lithium in hexane was slowly added to the cold solution while the temperature was maintained below 0° C. When the addition was completed, the reaction mixture was stirred for 4 hours at 0° C. Then 10.8 g (76 mmoles) of methyl iodide were added, the temperature was maintained at 0°–5° C. The resulting mixture was stirred for 16 hours at 0° C. and then poured into water and extracted with ethyl acetate (3.1 l). The combined extracts were dried and the solvent was removed. The residue purified by column chromatography on 450 g of silica gel, using hexane as eluant afford the pure 4,6-dimethyl-N-(α-phenylethyl)phenoxazine, as an oil, ir: 3837, 2940, 1640, 1600, 1570, 1470 cm$^{-1}$: nmr: (CDCl$_3$) 1.90–1.83 ppm (d, 3H), 2.23 ppm (s, 6H), 5.20 ppm (c, 1H), 6.40–6.16 ppm (m, 2H), 6.80–6.53 ppm (m, 4H), 7.53–7.20 ppm (m, 5H).

B. Similarly, by following the procedure of Part A of this Example, but replacing methyl iodide with:
- carbon dioxide (as either gas bubbled through or solid added to the solution);
- trimethylchorosilane;
- dimethyldisulfide;
- dimethylformamide;
- ethyliodide;
- di-n-hexyliodide;
- diethyldisulfide;
- di-n-hexyldisulfide;
- N,N-dimethylacetamide one can obtain:
- 4,6-dicarboxylic acid-N-(α-phenylethyl)phenoxazine, mp 346° C. (dec);

4,6-bis(trimethylsilyl)-N-(α-phenylethyl)phenoxazine;
4,6-dimethylthio-N-(α-phenylethyl)phenoxazine, (oil) ir: 2940, 1610, 1580, 1555, 1460 cm$^{-1}$: nmr: (CDCl$_3$) 1.90–1.80 ppm (d, 3H), 2.50 ppm (s, 6H), 5.36 ppm (c, 1H), 6.36–6.16 ppm (m, 2H), 6.73–6.60 ppm (m, 3H), 7.47–7.20 ppm (m, 6H);
4,6-diformyl-N-(α-phenylmethyl)phenoxazine, mp 181°–182° C.;
4,6-diethyl-N-(α-phenylethyl)phenoxazine;
4,6-di-n-hexyl-N-α-phenylethyl)phenoxazine;
4,6-bis(ethylthio)-N-(α-phenylethyl)phenoxazine;
4,6-bis(n-hexylthio)-N-(α-phenylethyl)phenoxazine; and
4,6-acetyl-N-(α-phenylethyl)phenoxazine.

C. Similarly, by following the procedure of Part A of this Example, but replacing:
N-(α-phenylethyl)phenoxazine with;
N-t-butyldimethylsilylphenoxazine, and replacing methyl iodide with:
  carbon dioxide (as either gas bubbled through or solid added to the solution);
  trimethylchorosilane;
  methyldisufide;
  dimethylformamide;
  ethyliodide;
  n-hexyliodide;
  diethyldisufide;
  di-n-hexyldisulfide;
  N,N-dimethylacetamide one can obtain:
N-(t-butyldimethylsilyl)phenoxazine-4,6-dicarboxylic acid;
4,6-bis(trimethylsilyl)-N-(t-butyldimethylsilyl)phenoxazine;
4,6-bis(methylthio)-N-(t-butyldimethylsilyl)phenoxazine;
4,6-diformyl-N-(t-butyldimethylsilyl)phenoxazine;
4,6-diethyl-N-(t-butyldimethylsilyl)phenoxazine;
4,6-di-n-hexyl-N-(t-butyldimethylsilyl)phenoxazine;
4,6-bis(ethylthio)-N-(t-butyldimethylsilyl)phenoxazine;
4,6-di-n-hexylthio-N-(t-butyldimethylsilyl)phenoxazine; and
4,6-di-acetyl-N-(t-butyldimethylsilyl)phenoxazine.

EXAMPLE 15

4,6-(Dihydroxymethyl)-N-(α-phenylethyl)phenoxazine

A. 822 Milligrams (21 mmoles) of sodium borohydride was added to a stirred suspension of 3 g of (8.7 mmoles) of 4,6-diformyl-N-(α-phenylethyl)phenoxazine (Example 10) in 100 ml of absolute ethanol. As the reaction proceeded the starting material went into solution. The reduction was complete in 15 minutes, as demonstrated by TLC analysis [hexane-ethyl acetate (6:4)]. The insoluble material was separated by filtration and the filtrate the solvent was removed to dryness. The residue was diluted with 100 ml of water and extracted with ethyl acetate (2×100 ml). The combined extracts were dried and the solvent was removed. The residue was purified by column chromatography on 120 g of silica gel using hexane-ethyl acetate (6:4) as eluant, thus obtaining the title compound, as an oil: ir: 3600, 3530, 3120, 2940, 1600, 1570, 1470 cm$^{-1}$: nmr: (CDCl$_3$) 1.90–1.83 ppm (d, 3H), 3.65 ppm (broad OH peak), 4.60 ppm (s, 4H), 5.23 ppm (c, 1H), 6.53–6.33 ppm (m, 2H), 6.76–6.66 ppm (m, 4H), 7.50–7.23 ppm (m, 5H).

EXAMPLE 16

4,6-Dihydroxymethylphenoxazine

A. A solution of 1 g (2.9 mmoles) of 4,6-diformyl)-N-(α-phenylethyl)phenoxazine in 50 ml of ethyl acetate and 20 ml of ethanol was added to a suspension of 1 g of 10% palladium-charcoal catalyst in 100 ml of absolute ethanol. The resulting mixture was hydrogenated at atmospheric pressure (585 mm Hg) for 21 hours. The catalyst was separated by filtration through celite and the the solvent was removed under reduced pressure. The residue was purified by column chromatography on 40 g of silica gel, eluting the product with ethyl acetate, thus obtaining the title compound which was recrystallized from ethyl acetate:hexane, mp 183°–184° C. (dec).

B. Similarly, by following the procedure of Part A above, but replacing 4,6-diformyl-N-(α-phenylethyl)phenoxazine with:
  4,6-dimethyl-N(α-phenylethyl)phenoxazine one can obtain:
  4,6-dimethylphenoxazine, mp 150°–151° C.

EXAMPLE 17

Phenoxazine-4-6-dicarboxylic acid dimethyl ester

A. A suspension of 129 mg of phenoxazine-4-6-dicarboxylic acid in 10 ml of diethyl ether was treated dropwise with an ethereal solution of diazomethane, until the color of diazomethane persisted in the mixture. The solvent was removed under reduced pressure and the residue recrystallized from methylene chloride:hexane, to produce phenoxazine-4-6-dicarboxylic acid dimethyl ester in pure form, mp 145°–146° C.

EXAMPLE 18

4,6-Dimethylthiophenoxazine

A. 500 Milligrams of zinc dust was added to a stirred solution of 700 mg (1.8 mmoles) of:
4,6-dimethylthio-N-(α-phenylethyl)phenoxazine in 25 ml of glacial acetic acid. Thereafter, 2 ml of concentrated hydrochloric acid was added, in a dropwise fashion. The reaction was monitored by TLC [hexane-ethyl acetate (8:2)]. When the reaction was complete (in approximately 5 minutes) the mixture was diluted with 100 ml of water and extracted with 100 ml of ethyl acetate. The extract was washed 3 times with water, dried and the solvent was removed under reduced pressure. Purification of the residue on a 3 g silica gel column, using hexane-methylene chloride (8:2) as eluant afforded 4,6-dimethylthiophenoxazine, which was recrystallized from ethyl acetate:hexane, mp 140°–141° C.

B. Similarly, by following the procedure of Part A above, but replacing:
4,6-dimethylthio-N-(α-phenylethyl)phenoxazine with::
  4,6-bis(trimethylsilyl)-N-(α-phenylethyl)phenoxazine;
  4,6-dimethylthio-N-(α-phenylethyl)phenoxazine;
  4,6-diethyl-N-(α-phenylethyl)phenoxazine;
  4,6-di-n-hexyl-N-(α-phenylethyl)phenoxazine;
  4,6-diethylthio-N-(α-phenylethyl)phenoxazine;
  4,6-di-n-hexylthio-N-(α-phenylethyl)phenoxazine; and
  4,6-diacetyl-N-(α-phenylethyl)phenoxazine, one can obtain:
  4,6-bis(trimethylsilyl)phenoxazine;

4,6-bis(methylthio)phenoxazine, mp 140°-141° C.;
4,6-diethylphenoxazine;
4,6-di-n-hexylphenoxazine;
4,6-diethylthiophenoxazine;
4,6-di-n-hexylthiophenoxazine; and
4,6-diacetylphenoxazine.

EXAMPLE 19

4,6-Diformylphenoxazine

A. Tetrabutylammonium fluoride (0.746 g, 2.8 mmol) was dissolved in 1.5 ml of dry tetrahydrofuran and the solution was cooled to 0° C. To this stirred solution 4,6-diformyl-N-(t-butyldimethylsilyl)phenoxazine (0.841 g, 2.3 mmol) dissolved in dry tetrahydrofuran was added in a dropwise manner. Five minutes after the addition was completed the reaction was shown by TLC to be completed (silica gel, ethylacetate). The solution was then poured onto water, the precipitated solid collected by filtration and dried in vacuo. The product had a melting point of 266°-267° C. after crystallization from ethyl ether:hexane.

B. Similarly, by following the procedure of Part A above, but replacing:
4,6-diformyl-N-(t-butyldimethylsilyl)phenoxazine with:
  N-(t-butylmethylsilyl)phenoxazine-4,6-dicarboxylic acid;
  4,6-bis(trimethylsilyl)-N-(t-butyldimethylsilyl)-phenoxazine;
  4,6-bis(methylthio)-N-(t-butyldimethylsilyl)phenoxazine;
  4,6-diethyl-N-(t-butyldimethylsilyl)phenoxazine;
  4,6-di-n-hexyl-N-(t-butyldimethylsilyl)phenoxazine;
  4,6-bis(ethylthio)-N-(t-butyldimethylsilyl)phenoxazine;
  4,6-di-n-hexylthio-N-(t-butyldimethylsilyl)phenoxazine; and
  4,6-di-acetyl-N-(t-butyldimethylsilyl)phenoxazine, one can obtain:
    phenoxazine-4,6-dicarboxylic acid, mp 146° C.;
    4,6-bis(trimethylsilyl)phenoxazine;
    4,6-bis(methylthio)phenoxazine, 140°-141° C.;
    4,6-diethyl-phenoxazine;
    4,6-di-n-hexyl-phenoxazine;
    4,6-bis(ethylthio)phenoxazine;
    4,6-di-n-hexylthiophenoxazine; and
    4,6-di-acetyl-phenoxazine

EXAMPLE 17

The following example illustrates the preparation of representative pharmaceutical formulations containing an active compound of formula I, e.g., 4,6-formyl-phenoxazine.

| I.V. Formulation | |
|---|---|
| Active compound | 0.14 g |
| Propylene glycol | 20.0 g |
| POLYETHYLENE GLYCOL 400 | 20.0 g |
| TWEEN 80 | 1.0 g |
| 0.9% Saline solution | 100.0 ml |

Other compounds of Formula A and the pharmaceutically acceptable salts thereof may be substituted therein.

EXAMPLE 18

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 19

| Ingredients | Quantity per capsule, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 20

| Ingredients | Quantity per tablet, mgs. |
|---|---|
| Active ingredient | 1 |
| cornstarch | 50 |
| lactose | 145 |
| magnesium stearate | 5 |

The above ingredients are mixed intimately and pressed into single scored tablets.

EXAMPLE 21

Topical Formulation

This formulation is a variation of Beeler's Base (See Remington's Pharmaceutical Sciences, 15th Ed., p. 1534)

| Active ingredient | 1 g |
|---|---|
| Cetyl Alcohol | 15 g |
| White Wax | 1 g |
| Propylene Glycol | 10 g |
| Sodium lauryl Sulfate | 2 g |
| Water | 72 g |

The cetyl alcohol, white wax and active ingredient are heated together at about 65° C. in propylene glycol. The sodium lauryl sulfate and water are mixed together. The two solutions are then mixed together, and stirred well. The well mixed solution is removed from the heat and mixed to the point of congealing.

EXAMPLE 22

| Ingredients | Quantity per tablet, mgs. |
|---|---|
| Active ingredient | 150 |
| lactose | 92 |

The above ingredients are mixed and introduced into a hard-shell gelatin tablet.

EXAMPLE 23

An injectable preparation buffered to a pH of 7 is prepared having the following composition:

| Ingredients | |
|---|---|
| Active ingredient | 0.2 g |
| KH$_2$PO$_4$ buffer (0.4 M solution) | 2 ml |
| KOH (1 N) | q.s. to pH 7 |
| water (distilled, sterile) | q.s. to 20 ml |

EXAMPLE 24

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 25

Conversion of Phenoxazine-4,6-dicarboxylic acid

Sodium methoxide (82 mg) is added to a solution of phenoxazine 4,6-dicarboxylic acid in methanol (5 ml). The solution is then evaporated to dryness to afford phenoxazine 4,6-dicarboxylic acid sodium salt. This compound may be converted to salts such as potassium, lithium, ammonium, calcium, magnesium, ferrous, zinc, copper, manganous, aluminum, ferric, manganic salts and the like using similar methods.

EXAMPLE 26

Conversion of Phenoxazine-4,6-dicarboxylic acid sodium salt into phenoxazine-4,6-Dicarboxylic acid A two-fold stoichiometric excess of 1N hydrochloric acid is added to a solution of phenoxazine-4,6-dicarboxylic acid sodium salt in water. The solution is then extracted with ether, and the extract is dried and the solvent removed under reduced pressure to afford phenoxazine-4,6-dicarboxylic acid.

EXAMPLE 27

Assay for Inhibition of Lipoxygenase Activity By Human Polymorphonuclear Leukocytes Experimental Procedures 1. Preparation of the cells: The PMNs are prepared from 200–300 ml of heparinized blood of healthy donors not receiving any medication for at least 7 days using Ficol-Hypaque gradients. In general, PMNs are greater than 90% pure and their viability is assessed by dye-exclusion to be better than 95%. The cells are suspended in phosphate buffered saline containing 1.0 mM CaCl$_2$ (pH 7.4) and 0.1% ovalbumin, and used within 30 minutes.

2. Lipoxygenase Assay: Incubations are carried out at 37° C. for 5 minutes in a total volume of 0.2 ml arachidonic acid 1-C$^{14}$ (1 × 10$^{-4}$M unless otherwise indicated, and approximately 300,000 cpm) is added to a suspension of cells (approximately 5 × 10$^6$) to initiate the reaction. Prior to the addition of above substrate, the test substances are added to the cells at appropriate concentrations and preincubated at 37° C. for 5 minutes. In general, stock solutions of test substances are prepared in ethanol (or other appropriate solvents) and diluted with either incubation-buffer or water. The final concentration of ethanol in the incubation did not exceed 1%. Boiled enzyme blanks and controls containing no test compound are always included. The incubations are terminated by the addition of 0.6 ml of methanol, vortexed and kept on ice for 30 minutes.

1.6 ml of deionized water is added, vortexed, centrifuged, the supernatants decanted and kept in the freezer overnight. Separation of arachidonic acid and lipoxygenase products are carried out using "Baker" disposable C$^{-18}$ extraction columns (1 ml capacity). The columns are prewashed with MeOH (2.0 ml) followed by deionized water (2 ml). After most of the solvent is removed, 2.0 ml of the supernatant is applied to the extraction columns and the solvent is allowed to flow through. The columns are then washed with 5 ml of deionized water and the eluate is discarded. The columns are then eluted with 6.0 ml of a solvent mixture (acetonitrite:H$_2$O:acetic acid in the proportion 50:50:0.1) which recovers all the arachidonic acid metabolites including 5-HETE and LTB, with very little of arachidonic acid (AA) being eluted (less than 2–3% of incubated counts). The columns are then eluted with 2.0 ml of methanol (forced through by N$_2$) which elutes all of the unreacted substrate AA. The eluates are collected in scintillation vials and 1.0 ml aliquot from each of the two fractions are counted for radioactivity in a Packard liquid scintillation counter. From the radioactivity data thus obtained percent yields of total lipoxygenase products in blanks, controls and drug containing tubes are calculated as well as percent inhibition by the test compounds.

While the present invention has been described with reference to the specific embodiments thereof, it should be understood by those skilled in this art that various changes may be made and equivalents may be substituted without departing from the true spirit and scope of the invention. In addition, many modifications may be made to adopt a particular situation, material, or composition of matter, process, process step or steps, or the present objective to the spirit and scope of the invention. In addition, many modifications may be made to adopt a particular situation, material, or composition of matter, process, process step or steps, or the present objective to the spirit of this invention without departing from its essential teachings.

What is claimed is:

1. A compound represented by the formula:

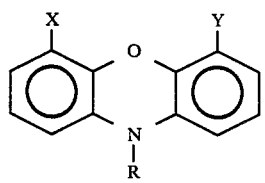

where:

R is an α-phenylethyl protecting group;

X is alkyl, hydroxyalkyl, alkylthio, haloalkyl, C(O)R$^1$, CH$_2$NR$^2$R$^3$, or Si(R$^4$)$_2$R$^5$; where:

R¹ is hydrogen, hydroxy, alkyl, alkoxy, aryl, aryloxy, or amino;

R² and R³ are independently hydrogen or alkyl, or NR²R³ together represent a heterocyclic ring having from four to seven members and containing no more than one hetero-atom additional to the nitrogen of NR²R³;

R⁴ is lower alkyl or phenyl; and

R⁵ is lower alkyl;

Y is the same as X or hydrogen; or a pharmaceutically acceptable salt thereof.

2. The compound of claim 1 wherein Y is hydrogen.

3. The compound of claim 2 wherein X is methyl.

4. The compound of claim 2 wherein X is chloromethyl.

5. The compound of claim 2 wherein X is methylthio.

6. The compound of claim 2 wherein X is formyl.

7. The compound of claim 2 wherein X is hydroxymethyl.

8. The compound of claim 2 wherein X is dimethylaminomethyl.

9. The compound of claim 2 wherein X is carboxyl.

10. The compound of claim 2 wherein X is N-piperidinylmethyl.

11. The compound of claim 2 wherein X is N-morpholinomethyl.

12. The compound of claim 1 wherein Y is the same as X.

13. The compound of claim 12 wherein X is methyl.

14. The compound of claim 12 wherein X is chloromethyl.

15. The compound of claim 12 wherein X is methylthio.

16. The compound of claim 12 wherein X is formyl.

17. The compound of claim 12 wherein X is hydroxymethyl.

18. The compound of claim 12 wherein X is dimethylaminomethyl.

19. The compound of claim 12 wherein X is carboxyl.

20. A method of preparing a 4-monosubstituted or 4,6-disubstituted phenoxazine, wherein said method comprises removing a N-α-phenylethyl protecting group from the corresponding N-α-phenylethyl-protected compound.

21. The method of claim 20, wherein said 4-monosubstituted or 4,6-disubstituted phenoxazine is of the formula:

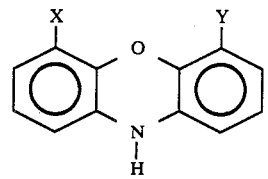

where:

X is alkyl, hydroxyalkyl, alkylthio, haloalkyl, C(O)R¹, CH₂NR²R³, or Si(R⁴)₂R⁵; where:

R¹ is hydrogen, hydroxy, alkyl, alkoxy, aryl, aryloxy, or amino;

R² and R³ are independently hydrogen or alkyl, or NR²R³ together represent a heterocyclic ring having from four to seven members and containing no more than one hetero-atom additional to the nitrogen of NR²R³;

R⁴ is lower alkyl or phenyl; and

R⁵ is lower alkyl;

Y is the same as X or hydrogen; or a pharmaceutically acceptable salt thereof.

* * * * *